United States Patent [19]

Edmundson et al.

[11] Patent Number: 4,873,078

[45] Date of Patent: Oct. 10, 1989

[54] HIGH-GLOSS, HIGH-SHINE LIPSTICK

[75] Inventors: Robert J. Edmundson, Germantown; Terry C. Jacks, Memphis, both of Tenn.

[73] Assignee: Plough, Inc., Memphis, Tenn.

[21] Appl. No.: 184,995

[22] Filed: Apr. 22, 1988

[51] Int. Cl.⁴ .................. A61K 7/027; A61K 7/025
[52] U.S. Cl. ............................. 424/64; 424/DIG. 5
[58] Field of Search ..................... 424/64, DIG. 5; 514/789

[56] References Cited

U.S. PATENT DOCUMENTS

| | | | |
|---|---|---|---|
| 3,148,125 | 9/1964 | Strianse et al. | 424/64 |
| 3,201,314 | 8/1965 | Morshauser et al. | 424/64 |
| 3,818,105 | 6/1974 | Coopersmith et al. | 514/789 |
| 3,957,969 | 5/1976 | Fujiyama et al. | 424/64 |
| 4,781,917 | 11/1988 | Luebbe et al. | 514/949 X |

Primary Examiner—Ellis P. Robinson
Assistant Examiner—Susan S. Rucker
Attorney, Agent, or Firm—Thomas D. Hoffman; Gerald S. Rosen

[57] ABSTRACT

A lipstick composition comprising a gloss-enhancing amount i.e. about 0.5 to about 8 weight percent of isohexadecane in a conventional lipstick formulation is disclosed.

7 Claims, No Drawings

HIGH-GLOSS, HIGH-SHINE LIPSTICK

BACKGROUND OF THE INVENTION

This invention relates to a lipstick composition containing a gloss-enhancing amount of isohexadecane in admixture with a conventional lipstick formulation. This invention particularly relates to an integral multi-colored lipstick composition comprising a gloss-enhancing amount of isohexadecane in admixture with lipstick formulation containing a heterogeneous mixture of at least two distinctly different dyes.

Lipstick is a molded, solid fatty base containing dissolved and suspended dyes, preservatives, fragrance in admixture with cosmetically acceptable waxes, oils, solids and semisolids. M. G. deNavarre in chapter 44 entitled "Lipstick" of "The Chemistry and Manufacture of Cosmetics", Vol. IV, 2nd Edition, Continental Press, 1975, p 767–840 discloses at page 769 the six most important base materials, excluding dyes preservative and fragrance, are the cosmetic waxes: beeswax, Candelilla wax, Carnauba wax and ozokerite as well as the cosmetic oils: castor oil and lanolin. deNavarre discloses that beeswax adds binding and molding properties to lipstick, Candellila wax gives lipstick hardness, rigidity and high gloss and Carnauba wax and ozokerite give molded lipstick toughness; castor oil is solvent for the dyes as well as acting as an emollient; and lanolin aids in making and maintaining molded lipstick as a homogeneous mass as well as serving as an emollient. Among the other numerous materials useful for a lipstick, deNavarre discloses that branched chain compounds such as fatty alcohols and fatty acid esters have been found to be useful in cosmetic products because of the ability of such branched-chain compounds to maintain a porous fatty film on the lips. However, branched-chain alkanes and alkenes such as pristane and squalene, respectively have not been found useful in cosmetics.

There is no disclosure that isohexadecane would be a gloss-enhancing agent in a lipstick. Isohexadecane is not listed in the third edition of the CTEA Cosmetic Ingredient Dictionary.

SUMMARY OF THE INVENTION

We have discovered that admixing a gloss-enhancing amount of isohexadecane with a conventional lipstick formulation surprisingly produces a high-gloss, high-shine lipstick. Thus, the present invention provides a lipstick composition comprising a gloss-enhancing amount of isohexadecane and a lipstick formulation. In a preferred aspect, the present invention provides an integral multi-colored lipstick composition comprising a gloss-enhancing amount of isohexadecane in admixture with a lipstick formulation containing a heterogeneous mixture of at least two distinctly different colored dyes.

DETAILED DESCRIPTION OF THE INVENTION

Isohexadecane is available from The Permethyl Corporation, 15 Lee Blvd., Frazer, Pa. 19355 under the tradename Permethyl® 101A.

By the term "a gloss-enhancing amount of isohexadecane" is meant about 0.5% to about 8% by weight of the lipstick composition, preferably about 3.5% to about 5.0% by weight should be isohexadecane.

We have discovered that by lowering the amount of castor oil in the lipstick formulation and adding a gloss-enhancing amount of isohexadecane in accordance with this invention, a high shine, high gloss lipstick composition results. The lipstick composition prepared in accordance with the present invention exhibit higher gloss and higher shine than conventional prior art lipsticks of similar composition which do not contain a gloss-enhancing amount of isohexadecane. The present invention is not limited to use in any one lipstick formulation but includes use in conventional lipstick formulations containing cosmetically acceptable waxes, oils, solid and semisolids in admixture with FDA-approved dyes, and optionally one or more preservatives antioxidants and preservatives.

Typical suitable cosmetic waxes include ozokerite, lanolin alcohol, paraffin wax, bayberry wax, Polawax (a reaction production of higher fatty alcohols and ethylene oxide available from Croda, Inc., New York, N.Y. 10016), trihydroxystearin, lanolin wax, beeswax, beeswax substitute (a mixture of paraffin and candellila wax and hydrogenated tallon glycerides and stearic acid and celylalcohol, available from Frank B. Ross Co., Inc., 6–10 Ash Street, Jersey City, N.J. 07304), Candellila wax, microcrystalline wax, Carnauba wax, stearyl alcohol, spermaceti, cocoa butter, fatty acids of lanolin, mono-, di- and triglycerides which are solid at 25° C., e.g., glyceryl tribehenate, a triester of behenic acid and glycerine and $C_{18}$–$C_{36}$ acid triglyceride, a mixture of triesters of $C_{18}$–$C_{36}$ carboxylic acids and glycerine available from Croda, Inc., New York, N.Y. under the tradenames Syncrowax HRC and Syncrowax HGL-C, respectively, fatty esters which are solid at 25° C., silicone waxes such as methyloctadecane-oxypolysiloxane and poly (dimethylsiloxy) stearoxysiloxane stearyl monoand diethanolamide, rosin and its derivatives such as the abietates of glycol and glycerol, hydrogenated oils solid at 25° C., and sucroglycerides.

Typical suitable cosmetic oils include mineral oil, Purcellin oil, perhydrosqualene, castor oil, polybutene, odorless mineral spirits, sweet almond oil, avocado oil,, calophyllum oil, ricin oil, vitamin E acetate, olive oil, silicone oils such as dimethicone, dimethylpolysiloxane and cyclomethicone, linolenic alcohol, oleyl alcohol, the oil of cereal germs such as the oil of wheat germ, isopropyl palmitate, isopropyl myristate, butyl myristate, hexadecyl stearate, butyl stearate, decyl oleate, acetyl glycerides, the octanoates and benzoates of ($C_{12}$–$C_{15}$) alcohols, the octanoates and decanoates of alcohols and polyalcohols such as those of alcohols such as those of isopropyl adipate, hexyl laurate and octyl dodecanoate.

Typical suitable antioxidants include propyl octyl and dodecyl esters of gallic acid, butylated hydroxyanisole, i.e., BHS, which is a mixture of 3-tert-butyl-4-hydroxyanisole (major) and 2-tert-butyl-4-hydroxyanisole, butylated hydroxytoluene and nordihydroguaiaretic acid.

Typical suitable flavoring agents include those approved by The Fragrance Institute such as chocolate fudge flavor available from Noville Essential Oil Col., North Bergen, N.J. 07047 as well as others available from International Flavors and Frangrances, New York, N.Y.

Typical suitable sweeteners include sucrose, corn syrup, saccharin and asparatame. The sweeteners are normally dissolved in water and dipropylene glycol is added before use in lipstick compositions of the present invention.

Typical suitable cosmetic solids or semi-solids include lanolin, hydrogenated lanolin, hydroxylated lanolin, acetylated lanolin, petrolatum, isopropyl lanolate, cetyl myristate, myristyl myristate, myristyl lactate, cetyl alcohol, stearyl alcohol, isostearyl alcohol and isocetyl lanolate.

It is preferred to employ a mixture of these cosmetic ingredients for their different functions, for example oleyl alcohol is a penetrant and color vehicle, castor oil is a color dispersing agent, mineral oil and cyclomethicone are emollients and moisturizers.

Typical suitable preservatives include the lower alkyl esters of para-hydroxybenzoates (paraben) especially, methyl paraben, ethyl paraben, n-propyl paraben, n-butyl paraben, isobutyl paraben and mixtures thereof, imidazolidinyl urea, or diazolidinyl urea. The color pigments or coloring materials, e.g., organic dyes and inorganic pigments are usually dispersed in castor oil.

Typical suitable dyes employed in the cosmetic compositions of the present invention are the U.S. Government certified colors, both Drug and Cosmetic grade and Food, Drug and Cosmetic grade, e.g., D & C reds, oranges, yellows and blues. The pigments employed are generally inorganic pigments such as iron oxides, titanium dioxides, or other conventional pigments approved for cosmetic use. The dyes and pigments are preferably employed in an amount ranging from about 1% to about 10% by weight of the formulation with about 2% to about 4% being more preferred.

A lipstick base formulation may be prepared in a stirred tank to which is added a gloss-enhancing amount of isohexadecane and a mixture of cosmetically acceptable waxes, oils, solids and/or semi-solids, preferably free of dyes and pigments, preservatives and fragrance. If desired, different lipstick base formulations may be prepared for each separate dye or colorant to be used in the final lipstick composition. Regardless of how the lipstick based formulations are prepared, it is desirable that the base formulations for each different color have substantially similar consistencies to enable production of a uniform lipstick product when combined. After the base formulations are prepared, individual portions thereof are forwarded to separate color mixing tanks to which at least two distinctly different colored dyes and/or pigments are added, with mixing. After a homogeneous mixture is formed, flavoring and sweetener are added and mixing is continued until a homogeneous mixture is formed. The separate colored lipstick compositions may be then poured into molds. In a preferred aspect of this invention, lipstick compositions containing at least two distinctly different colored dyes and/or pigments are blended together under laminar-flow conditions in a funnel-shaped heterogeneous blender in accordance with the procedure of U.S. Pat. No. 3,201,314 at col. 2 lines 64 to col. 3 line 43, which is hereby incorporated by reference, to form an integral multi-colored lipstick.

The following example illustrates the invention. Definition and suppliers of the ingredients used may be found in the third edition of the CTFA Cosmetic Ingredients Dictionary, published by the Cosmetic, Toiletry, and Fragrance Association, Inc., 1110 Vermont Avenue, N.W., Washington, D.C. 20005 U.S.A. If any ingredients used in these examples are not available, substitutions may be made, since it is believed that the incorporation of the gloss-enhancing amount of isohexadecane will improve the shine and gloss when formulated into any conventional lipstick composition.

EXAMPLE 1

Fudge Swirl Lipstick

| Chocolate Brown Portion Ingredient | Weight Percent |
| --- | --- |
| Beeswax Substitute[1] | 7.200 |
| Candellila Wax SP | 5.000 |
| Carnuaba Wax SP | 4.400 |
| Ozokerite 170 MF | 1.400 |
| Acetylated Lanolin Alcohols | 14.900 |
| Hydrogenated Vegetable Oil | 7.000 |
| Lanolin Oil | 14.900 |
| Diisopropyl Dimerate | 1.750 |
| Mineral Oil, Light Carnation | 8.300 |
| Polybutene | 8.800 |
| Methyl Paraben | 0.100 |
| Propyl Paraben | 0.200 |
| Butyl Paraben | 0.100 |
| BHA | 0.050 |
| Part B | |
| Isohexadecane | 5.000 |
| Part C | |
| Extender Yellow #5 - (30%)[2] | 0.830 |
| Extender Red Oxide - (30%)[2] | 0.415 |
| Extender Red #7 - (30%)[1] | 0.707 |
| Extender Blue #1 - (30%)[1] | 0.269 |
| Extender Red #6 - (30%)[1] | 0.415 |
| Extender T1O$_2$ - (50%)[3] | 0.145 |
| Part D | |
| Fudge Chocolate Flavor | 4.000 |
| Part E | |
| Sacharin | 0.250 |
| Water | 0.350 |
| Dipropylene Glycol | 1.000 |
| Part F | |
| Castor Oil | 11.559 |

[1]paraffin and candelilla wax and hydrogenated tallow glycerides and stearic acid and cetyl alcohol.
[2]30% by weight in castor oil.
[3]50% by weight in castor oil.

[3]50% by weight in castor oil.

Melt all the solid ingredients of Part A in a steam-jacketed stainless steel kettle equipped with a double agitator stirrer at a temperature of 85° C.; add remaining ingredients in Part A and stir until a homogeneous mixture is formed. Add isohexadecane thereto and mix. Add to the so-formed mixture a mixture of the colors in Part C; stir until a homogeneous admixture is formed.

| White Portion Ingredient | Weight Percent |
| --- | --- |
| Beeswax Substitute | 7.200 |
| Candellila Wax SP | 5.000 |
| Carnuaba Wax SP | 4.400 |
| Ozokerite 170 MF | 1.400 |
| Acetylated Lanolin Alcohols | 14.900 |
| Hydrogenated Vegetable Oil | 7.000 |
| Lanolin Oil | 14.900 |
| Diisopropyl Dimerate | 1.750 |
| Mineral Oil, Light Carnation | 8.300 |
| Polybutene | 8.800 |
| Methyl Paraben | 0.100 |
| Propyl Paraben | 0.200 |
| Butyl Paraben | 0.100 |
| BHA | 0.050 |
| Part B | |
| Isohexadecane | 5.000 |
| Part C | |
| Extender, TiO$_2$ (50%)[1] | 1.500 |
| Part D | |
| Saccharin | 0.250 |
| H$_2$O | 0.350 |
| Dipropylene Glycol | 1.000 |
| Part E | |

-continued

| White Portion Ingredient | Weight Percent |
|---|---|
| Chocolate Fudge Flavor Part F | 4.000 |
| Castor Oil | 12.900 |

The procedure for the preparation of the brown portion outlined above was used to form the white portion.

The molten masses of the chocolate brown and white portions of the Fudge Swirl lipstick are blended together to produce a marbilized high gloss high shine lipstick. The blending is accomplished in the apparatus shown in FIG. 1 of U.S. Pat. No. 3,201,314 in accordance with the procedure described at Col. 2, line 64 of Col. 3, line 31 of U.S. Pat. No. 314 which is hereby incorporated by reference.

The brown-white marbilized lipstick so formed has higher-gloss and higher-shine on a visual comparison with a lipstick of similar composition without isohexadecane.

What is claimed is:

1. A lipstick composition comprising from about 0.5 to about 8 weight percent of isohexadecane in a lipstick formulation.

2. A lipstick composition of claim 1 wherein the lipstick formulation comprises at least two distinctly different colored dyes which are heterogeneously mixed to form a unitary lipstick composition.

3. A lipstick composition of claim 1 wherein the lipstick formulation further comprises a flavoring agent.

4. A lipstick composition of claim 1 comprising about 3.5 to about 5.0 weight percent of isohexadecane.

5. A lipstick composition of claim 1 comprising about 5 weight percent of isohexadecane.

6. An integral multi-colored lipstick composition comprising a gloss-enhancing amount of isohexadecane in admixture with a lipstick formulation containing a heterogeneous mixture of at least two distinctly different colored dyes.

7. A method of producing a high gloss lipstick which comprises admixing a lipstick formulation with about 0.5 to about 8 weight percent of isohexadecane.

* * * * *